(12) United States Patent
Ljungmann et al.

(10) Patent No.: US 6,436,348 B1
(45) Date of Patent: Aug. 20, 2002

(54) STAINING APPARATUS FOR PREPARATION OF TISSUE SPECIMENS PLACED ON MICROSCOPE SLIDES

(76) Inventors: Torstein Ljungmann, Geitemyrsveien 5, 0171 Oslo; Oystein Ljungmann, Elgfaret 15, N-1404 Siggerud, both of (NO)

( * ) Notice: Subject to any disclaimer, the term of this patent is extended or adjusted under 35 U.S.C. 154(b) by 0 days.

(21) Appl. No.: 09/529,170
(22) PCT Filed: Oct. 16, 1998
(86) PCT No.: PCT/NO98/00315
§ 371 (c)(1),
(2), (4) Date: Jun. 19, 2000
(87) PCT Pub. No.: WO99/20995
PCT Pub. Date: Apr. 29, 1999

(30) Foreign Application Priority Data

Oct. 16, 1997 (NO) .......................................... 19974780

(51) Int. Cl.⁷ ............................................... B32B 27/04
(52) U.S. Cl. ............................. 422/63; 422/65; 422/99; 422/67; 435/40.51; 118/423; 118/425
(58) Field of Search .............................. 422/65, 99, 63, 422/64, 67; 118/423, 425; 435/40.51

(56) References Cited

U.S. PATENT DOCUMENTS

| 5,573,727 | A | | 11/1996 | Keefe | |
|---|---|---|---|---|---|
| 6,017,495 | A | * | 1/2000 | Ljungmann | 422/65 |
| 6,110,425 | A | * | 8/2000 | Gao et al. | 422/66 |
| 6,180,061 | B1 | * | 1/2001 | Bogen et al. | 422/64 |
| 6,307,042 | B1 | * | 10/2001 | Goldberg et al. | 536/25.3 |
| 2001/0019703 | A1 | * | 9/2001 | Thiem et al. | 422/99 |

FOREIGN PATENT DOCUMENTS

| GB | 2196428 A | | 4/1988 | |
|---|---|---|---|---|
| NO | WO 97/19379 | * | 5/1997 | G02B/21/34 |

* cited by examiner

*Primary Examiner*—Jeffrey Snay
*Assistant Examiner*—Brian R Gordon
(74) *Attorney, Agent, or Firm*—Pitney, Hardin, Kipp & Szuch LLP

(57) ABSTRACT

A staining apparatus for preparation of tissue specimens placed on microscope slides, comprising a plurality of stations in the form of vessels having liquid baths for receiving baskets or suspensions receiving microscope slides with the topical specimens, a device for transporting each of the baskets/suspensions to respective stations to undergo a staining process, and a control unit for controlling the staining process in accordance with a chosen program. The apparatus is provided with a magazine for loading and simultaneous reception of a chosen number of baskets/suspensions with microscope slides, the magazine being provided with a device for heating of the baskets/suspensions placed in the magazine.

7 Claims, 6 Drawing Sheets

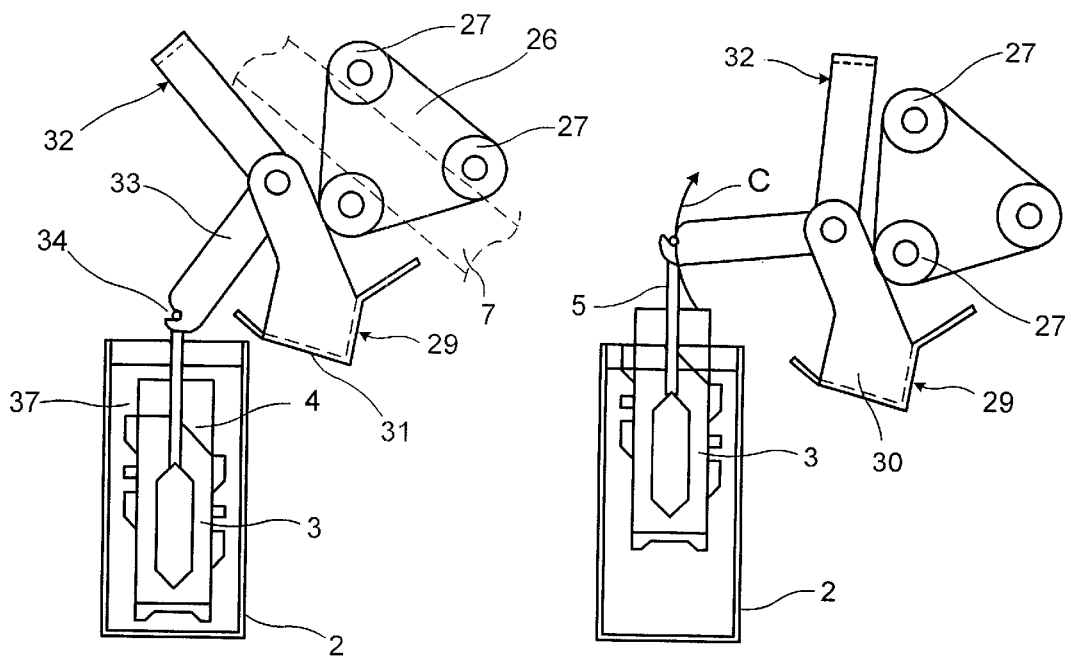
F I G. 7A     F I G. 7B
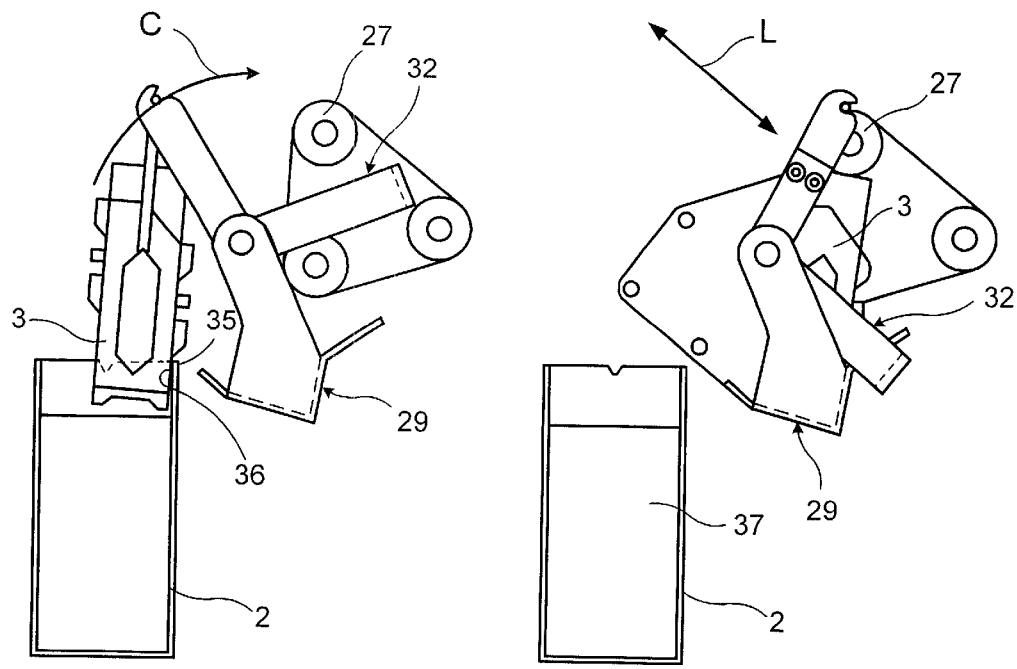
F I G. 7C     F I G. 7D

STAINING APPARATUS FOR PREPARATION OF TISSUE SPECIMENS PLACED ON MICROSCOPE SLIDES

BACKGROUND OF THE INVENTION

1. Field of the Invention

The invention relates to a staining apparatus for preparation of tissue specimens placed on microscope slides, comprising a plurality of stations in the form of vessels having liquid baths for receiving baskets or suspensions receiving microscope slides with the topical specimens, a means for transport of each of the baskets/suspensions to respective stations to undergo a staining process, and a control unit for controlling the staining process in accordance with a chosen program.

2. Description of the Prior Art

A staining apparatus of this type for example is known from U.S. Pat. No. 5,573,727, GB 2 196 428 A and international patent application No. PCT/NO96/00270 (WO 97/19379). For a further description of the construction and manner of operation of such an apparatus reference is made to these publications.

Such apparatuses stain both cytologic and histologic specimens according to different staining methods, depending on the type of tissue specimen that are to be stained.

SUMMARY OF THE INVENTION

In contradistinction to the cytologic specimens, the histologic specimens are embedded in advance in an embedment medium, such as paraffin, before they are cut into very thin slices of tissue specimens which are placed in a varying number on a microscope slide which is thereafter inserted into a basket or a suspension. A varying number of baskets or suspensions thereafter are placed in a heating stove to heat the microscope slides with tissue specimens to a desired temperature to melt down the embedment medium on the microscope slide, so that the tissue specimens will become stuck to the microscope slide during the transport from one bath to another during the subsequent staining process The basket (or suspension) with microscope slides thereafter is placed in a staining apparatus for staining of the tissue specimens in accordance with a program. The known staining apparatuses, e.g. the apparatus according to U.S. Pat. No. 5,537,727, is equipped with a means, e.g. a drawer, wherein one can load a basket and choose a staining program limited to one basket at a time, and moreover limited by the time factor for the working operation carried out by the transport means at this time. The distance back to the loading drawer to fetch a new basket, and the consideration for the programs of already loaded baskets if several baskets are in a staining process, the movement time of the conveyor between the different baskets, and the circumstance that two program steps can not be carried out at the same time, involves a substantial waiting time from the moment when the drawer is loaded with a basket and until the operator is able to load in the next basket.

Further, it is of substantial importance that the microscope slides, when they are placed in the bath in the staining apparatus which does not stain, but which removes superfluous embedment medium, shall have generally the same temperature as the temperature they had in the melting-down stove. The reason for this is that when the microscope slides lose their temperature, the process for removal of the embedment medium becomes more difficult and may take up to twice as long time. (A basket without heating takes about 8 min. as compared to about 3 min. with heating.)

The known staining apparatuses with the capacity of today are not able to take into consideration the fact that the microscope slides, when they are placed in the staining apparatus, should have the same temperature as the chosen temperature in the melting-down stove, or to compensate for the fact that the temperature of the microscope slides vary, so that the process for removal of the embedment medium can be carried out in an efficient manner. This means that the operator of the apparatus has to spend time to see to it that the basket with microscope slides is sufficiently heated when it is loaded into the staining apparatus, and thereafter has to wait an additional time before a new basket can be loaded in. This entails a waste of working resources because of much waiting time when loading more than one basket with microscope slides, and because of the manual handling of the baskets from the melting-down stove and into the staining apparatus.

The object of the invention therefore is to provide a staining apparatus involving both a substantial work saving and a substantial time saving in the loading of baskets/suspensions into the apparatus.

The above-mentioned object is achieved with a staining apparatus of the introductorily stated type which, according to the invention, is characterized in that it comprises a magazine for loading and simultaneous reception of a chosen number of baskets/suspensions with microscope slides, the magazine being provided with a means for heating of the baskets/suspensions placed in the magazine.

An advantageous embodiment of the apparatus is characterized in that the heating means is arranged to be controlled by the control unit in accordance with the topical program.

By providing the staining apparatus with a magazine which can receive several baskets having associated individual programs at the same time, and which is provided with a heating means for obtaining as quickly as possible a desired temperature to melt down the embedment medium on the histological specimens, there is achieved that one does not need a separate process for preheating and melting down the embedment medium in a separate stove. This implies a substantial work and time saving, since otherwise one has to load the baskets one by one with intervals of several minutes before the apparatus can take care of the individual baskets.

The magazine has a heating chamber which is arranged such that the transport means is allowed to fetch the topical basket directly from the chamber in accordance with a given temperature and a given minimum time in compliance with different programs which also control the different steps of the basket in the process wherein removal of the embedment medium, staining of the tissue specimens and delivery of the basket take place. Since the time factor for how long the histological specimens are to remain in the heating chamber, is not limited to a maximum time, but only to a minimum time, this will give a software-wise possibility to optimalize coordination of the different programs in a quite unique manner, since several baskets with several programs will be able to be evaluated simultaneously to find the most efficient running scheme for the movements of the transport means in order to be able to prepare as many baskets as possible in compliance with the different chosen programs in the shortest possible time. the magazine will function as a loading buffer, and will be able to inform the operator when for example four new baskets can be loaded in.

The staining apparatus according to the invention also admits that the transport means can return to the magazine in the middle of the staining process with a basket at a time, and that the magazine can be heated and used as a customary heating station in the middle of a staining process before a staining bath in which it is appropriate to have heated tissue specimens.

For the histological specimens the magazine will function as a melting-down chamber for the embedment medium, whereas for the cytological specimens it will function as a mere buffer when loading more than one basket at a time. Since the cytological specimens are not damaged by being put into a heated magazine, the apparatus of course may also be arranged such that both histological and cytological specimens can be prepared in one and the same apparatus.

In an advantageous embodiment of the apparatus according to the invention, the transport means which brings the baskets from one bath to another in accordance with a program, is arranged such that it lifts the topical basket up from the vessel in question in a circular movement, so that excess liquid from the basket is simultaneously wiped off against an edge of the vessel. In this manner it is avoided that liquid from the bath is transferred to and mixed with the liquid in the next bath, or that such transfer in any case is reduced to a minimum. The construction suitably is carried out such that the basket is lifted laterally inwards towards a means having a tight bottom plate preventing dripping into other vessels during transport of the baskets, and which provides for additional removal of remaining excess liquid since the microscope slides will lie, laterally in contact with said bottom plate, in order to guide the liquid drops away from the microscope slides.

Delivery from the apparatus of a ready basket does not take place by means of a separate means for unloading, but in that the transport means brings the ready basket to a given position in the apparatus, from which the operator can take out the ready basket directly.

BRIEF DESCRIPTION OF THE DRAWINGS

The invention will be further described below in connection with an exemplary embodiment with reference to the drawings, wherein

FIGS. 7A–7D show a sequence of operational positions of parts of the transport means during lifting of a basket with microscope slides from a vessel with a liquid bath, as viewed in the direction of the arrow A in FIG. 6, and wherein parts of the transport means for the sake of distinctness are omitted.

DETAILED DESCRIPTION OF THE PREFERRED EMBODIMENT

Figure 1:
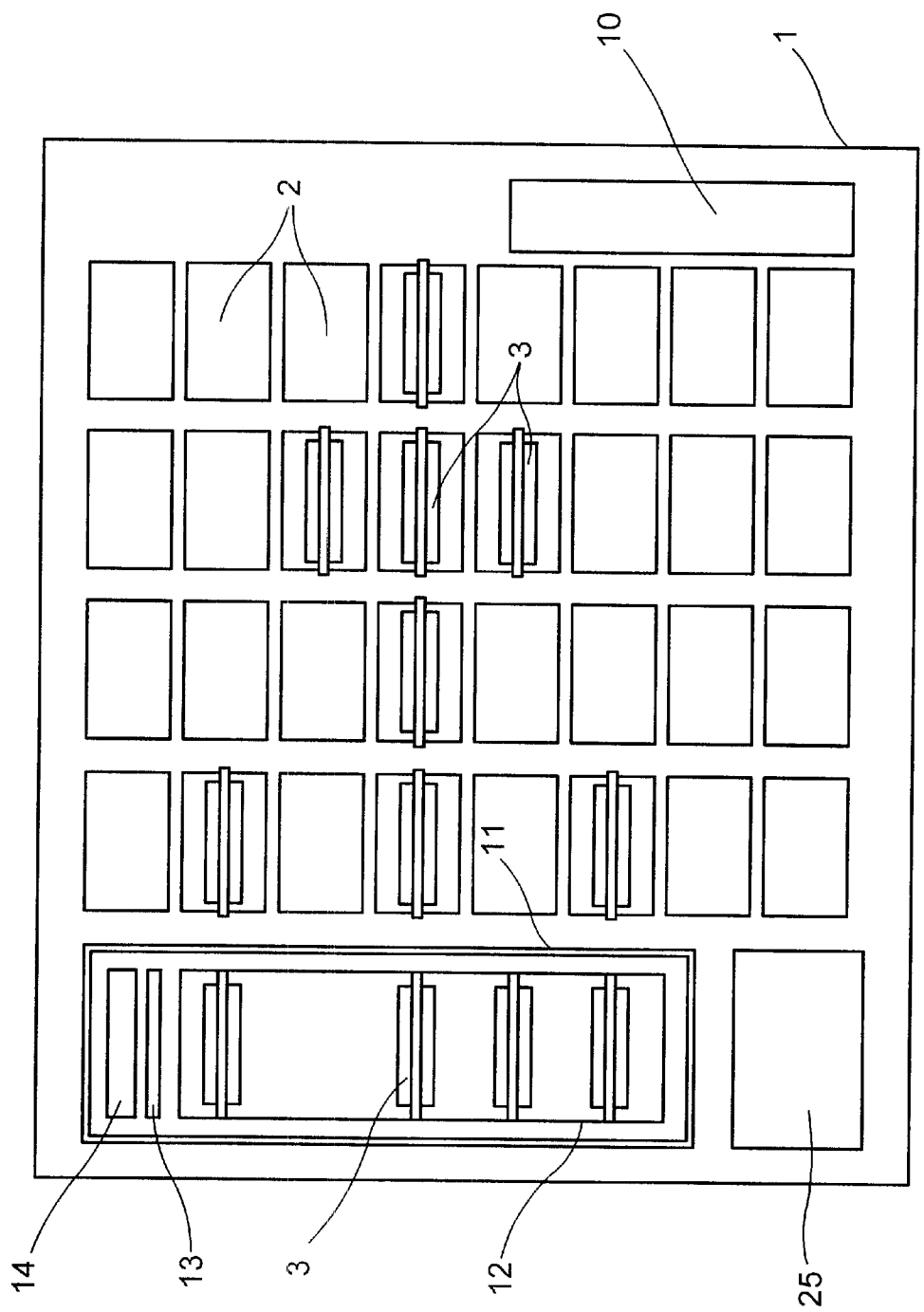
FIG. 1 shows a schematic plan view of an embodiment of a staining apparatus according to the invention.

The staining apparatus shown in the drawings has the same fundamental construction as that which is shown and described in the above-mentioned international patent application, that is, such that the stations of the apparatus with their vessels with liquid baths are arranged in a number of horizontal rows placed above one another on an inclined foundation like a tribune.

Figure 3:
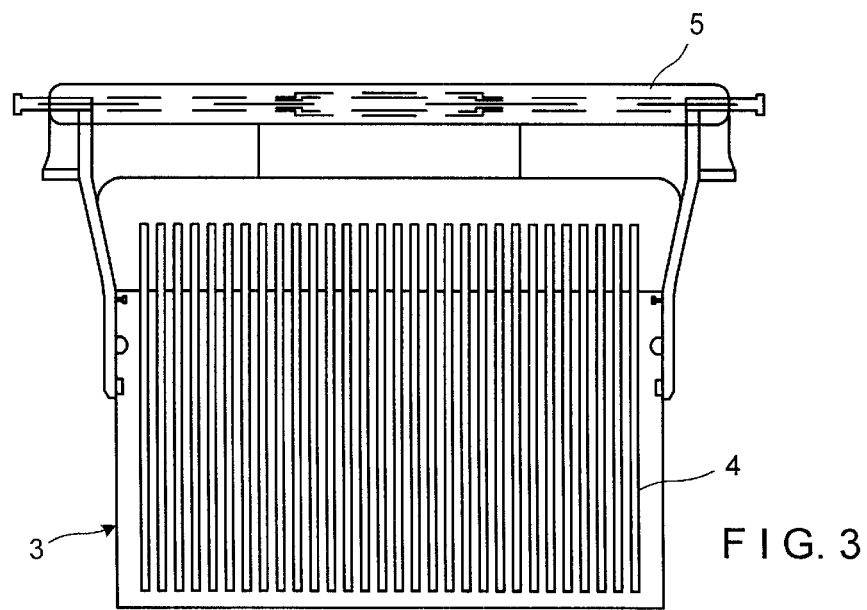
FIG. 3 shows a front view of a basket with microscope slides.

As shown, the apparatus or machine 1 comprises a number of rows and columns of working stations in the form of vessels 2 having liquid baths for receiving baskets 3 receiving microscope slides 4 with the topical tissue specimens. The vessels 2 are made of a transparent material, preferably glass. As shown in FIG. 3, each of the baskets are fixed to a suspension means 5 for suspension of the topical vessel 2. As an alternative, the microscope slides can be locked directly to a special suspension (not shown), the basket then being omitted. The baskets/suspensions are transported from bath to bath by a transport means or conveyor 6 which is movable back and forth along an inclined guide 7 by means of a motor. At its upper end the inclined guide is connected to a carriage 9 which is movable along a horizontal guide 8. Thus the movement of the conveyor takes place in a tribune plane, something which provides advantages which are further described in said patent application.

As mentioned, the baskets 3 (or the suspensions) are transported to respective stations/vessels 2 to go through a staining process in accordance with a chosen program. The apparatus comprises an electronic control unit, shown schematically at 10, for control of the operation of the apparatus in accordance with the topical program. The topical programs are stored in a programmable microprocessor.

Reference is made to the above-mentioned patent application for a further description of the general operation of the apparatus.

Figure 2:
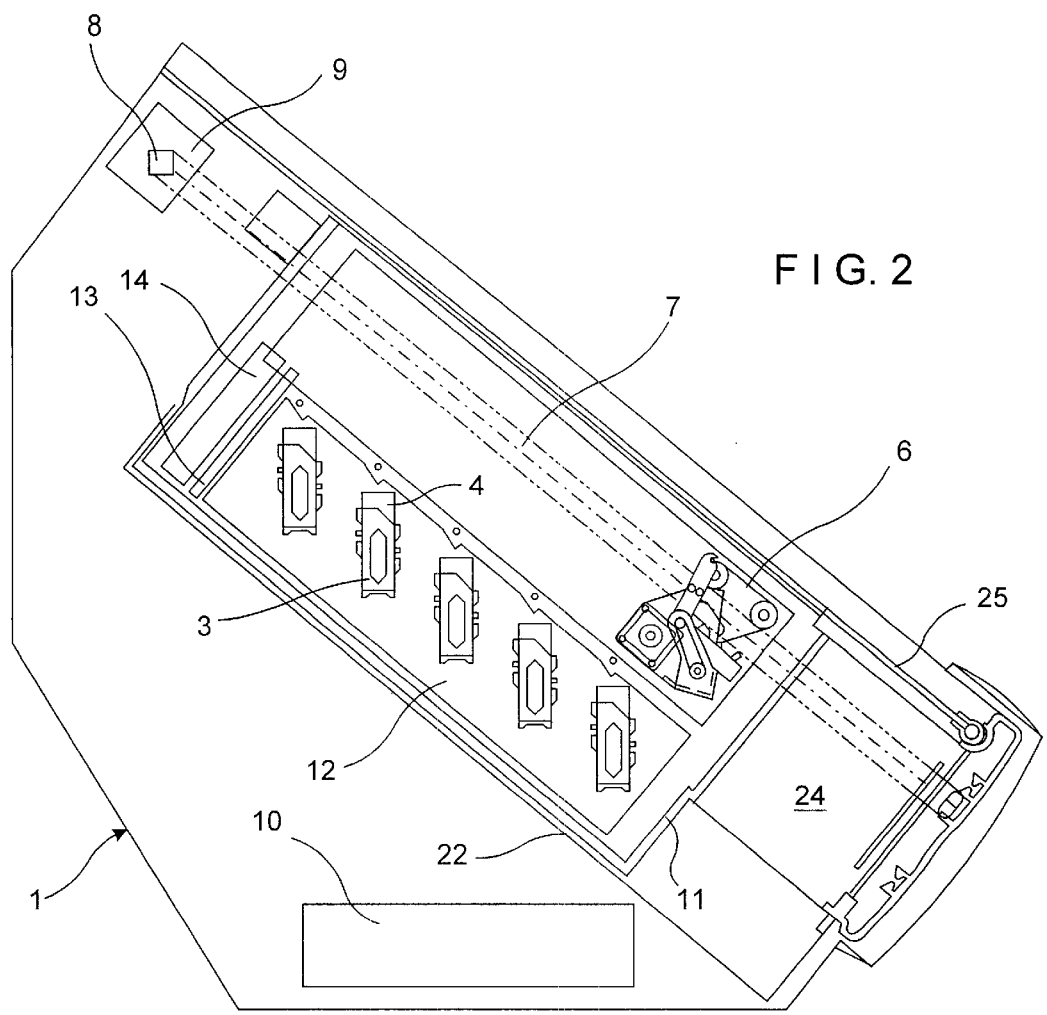
FIG. 2 shows a schematic sectional side view of the apparatus in FIG. 1.

In accordance with the invention the apparatus comprises a magazine for loading and simultaneous reception of a chosen number of baskets/suspensions with microscope slides. In the shown embodiment the magazine comprises a magazine housing 11 in which there is arranged a framework 12 for the support of baskets/suspensions 3. As appears from FIG. 2, the magazine in the shown embodiment can receive maximum five baskets. In the magazine housing there is arranged a heating means comprising a heating element 13 and a fan 14, where the fan is arranged to blow hot air towards baskets/suspensions placed in the magazine, for heating of these to a desired temperature. The heating means appropriately is arranged to be controlled by the control unit in accordance with the topical program.

As appears schematically from the drawings, the magazine housing 11 comprises longitudinally and transversely extending walls of which a longitudinally extending wall 15 which faces the stations/vessels 2 of the apparatus, in its upper portion is provided with a shutter or door 16 which, by means of a motor 17, can be opened and closed automatically when loading and unloading baskets/suspensions 3 by means of the conveyor 6. In connection with said loading and unloading the framework 12, which is arranged in the magazine housing 11, can be raised and lowered by means of a motor 18 which is coupled to the framework via a tooth belt means 19. The framework 12 is also raised to its upper position at the initial introduction or loading of baskets/suspensions into the magazine housing 11.

Figure 4:
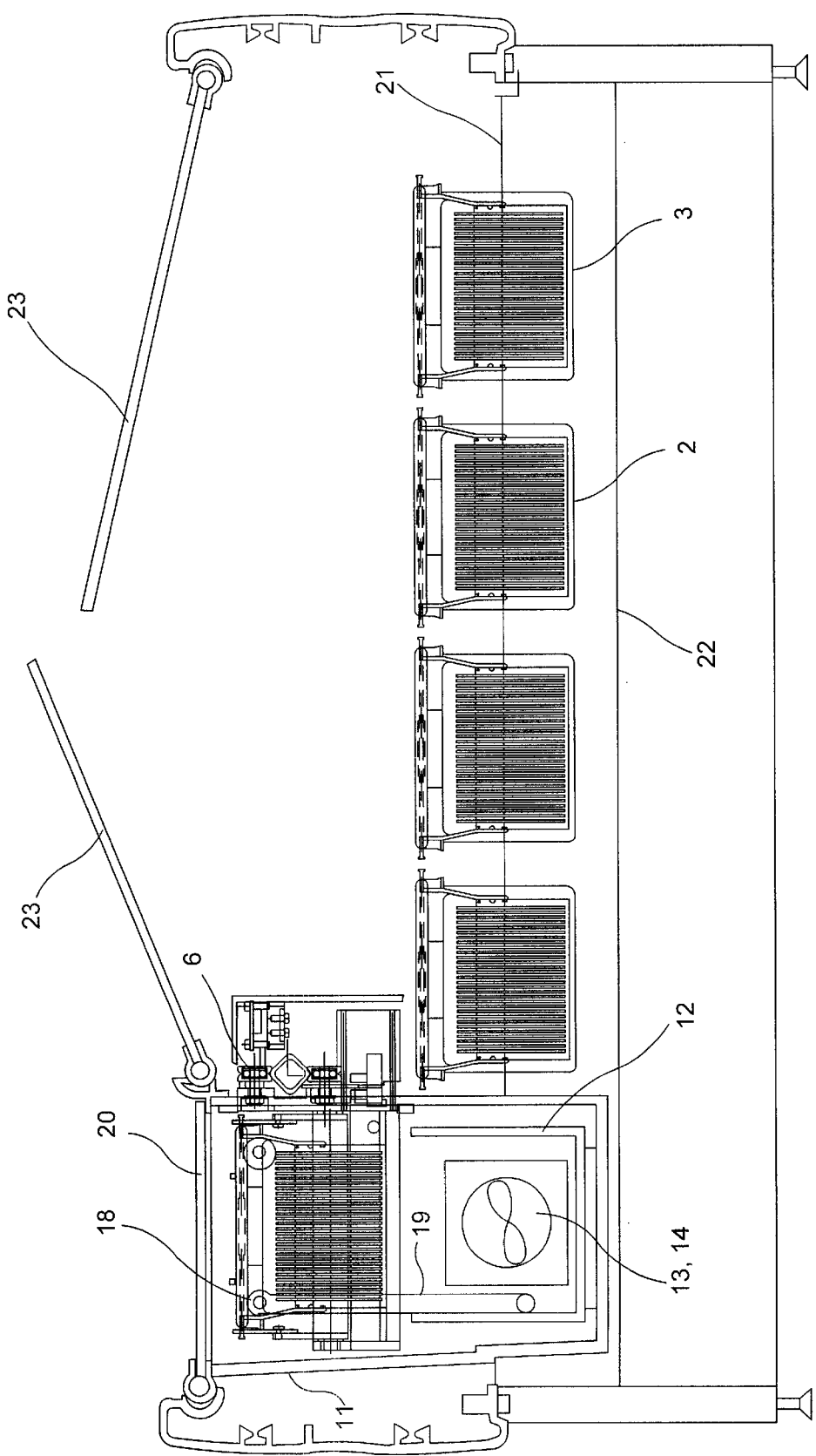
FIG. 4 shows a schematic sectional front view of the apparatus in FIG. 1.
Figure 5:
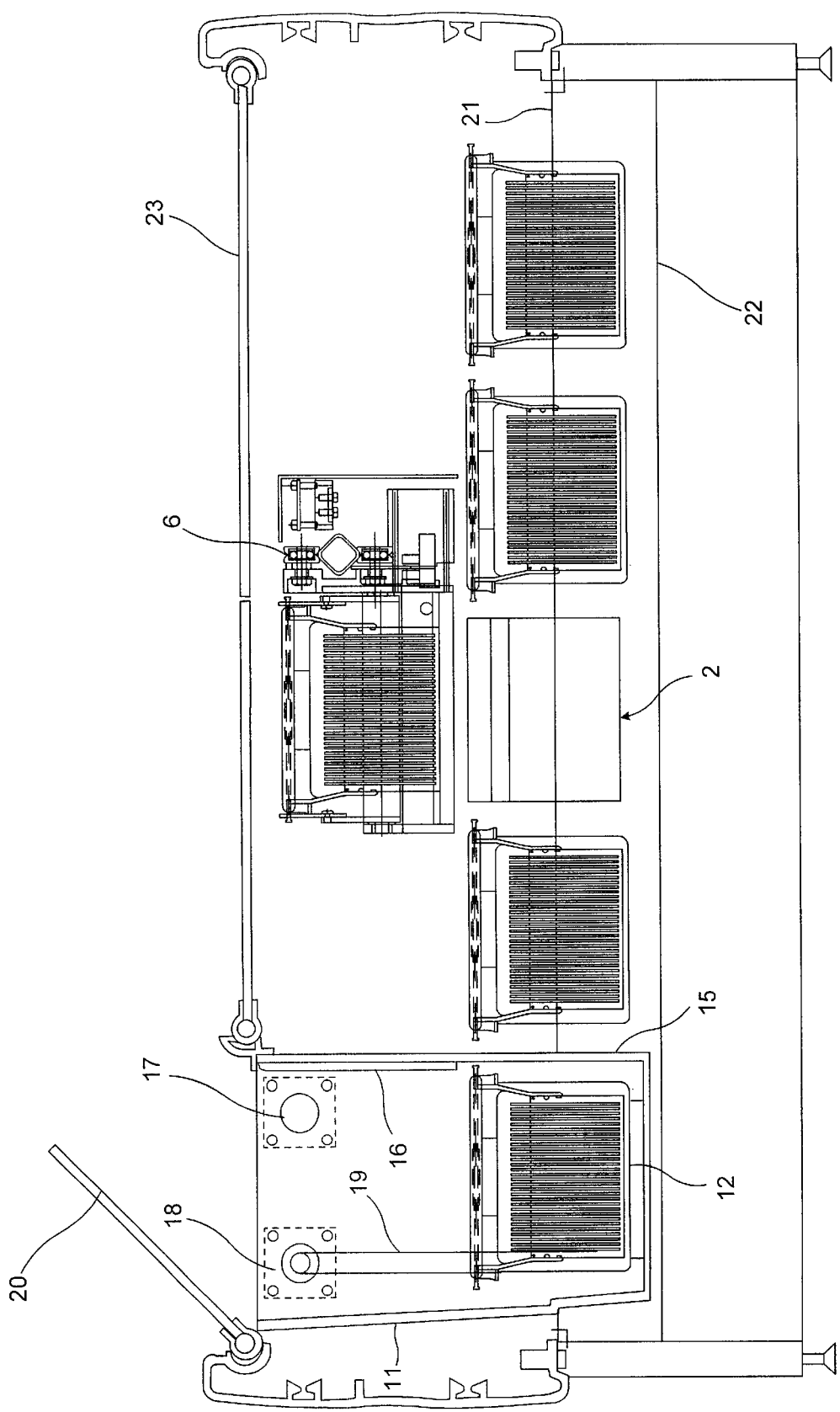
FIG. 5 shows a front view corresponding to FIG. 4, but with the transport means and a transported basket in another position than in FIGS. 4.

From FIGS. 4 and 5 it further appears that the magazine is provided with a lid 20 which is opened at the initial loading of baskets/suspensions with microscope slides. The baskets 2 and the magazine housing 11 are supported by a positioning or carrier plate 21 which is provided with adapted holes for receiving the baskets and the magazine housing, these being provided with outwards projecting flange portions (suggested for the magazine housing in FIGS. 2, 4 and 5) supported by the plate. A bottom box 22 is arranged beneath the carrier plate 21, for collection of liquid which may possibly come from the baths in the vessels or drip from baskets during transport thereof. Over the stations with the vessels 2 there is further shown to be arranged a bipartite lid 23 for access to the chemicals in the vessels.

When baskets/suspensions 3 with ready-treated microscope slides are to be delivered from the apparatus, this takes place in that the conveyor 6 brings a ready basket to a delivery position 24 where an operator can take out the basket directly from the conveyor. Thus, the apparatus has no special means for delivery of ready baskets. The unloading position 24 in FIG. 1 is shown to be covered by a lid 25.

Figure 6:
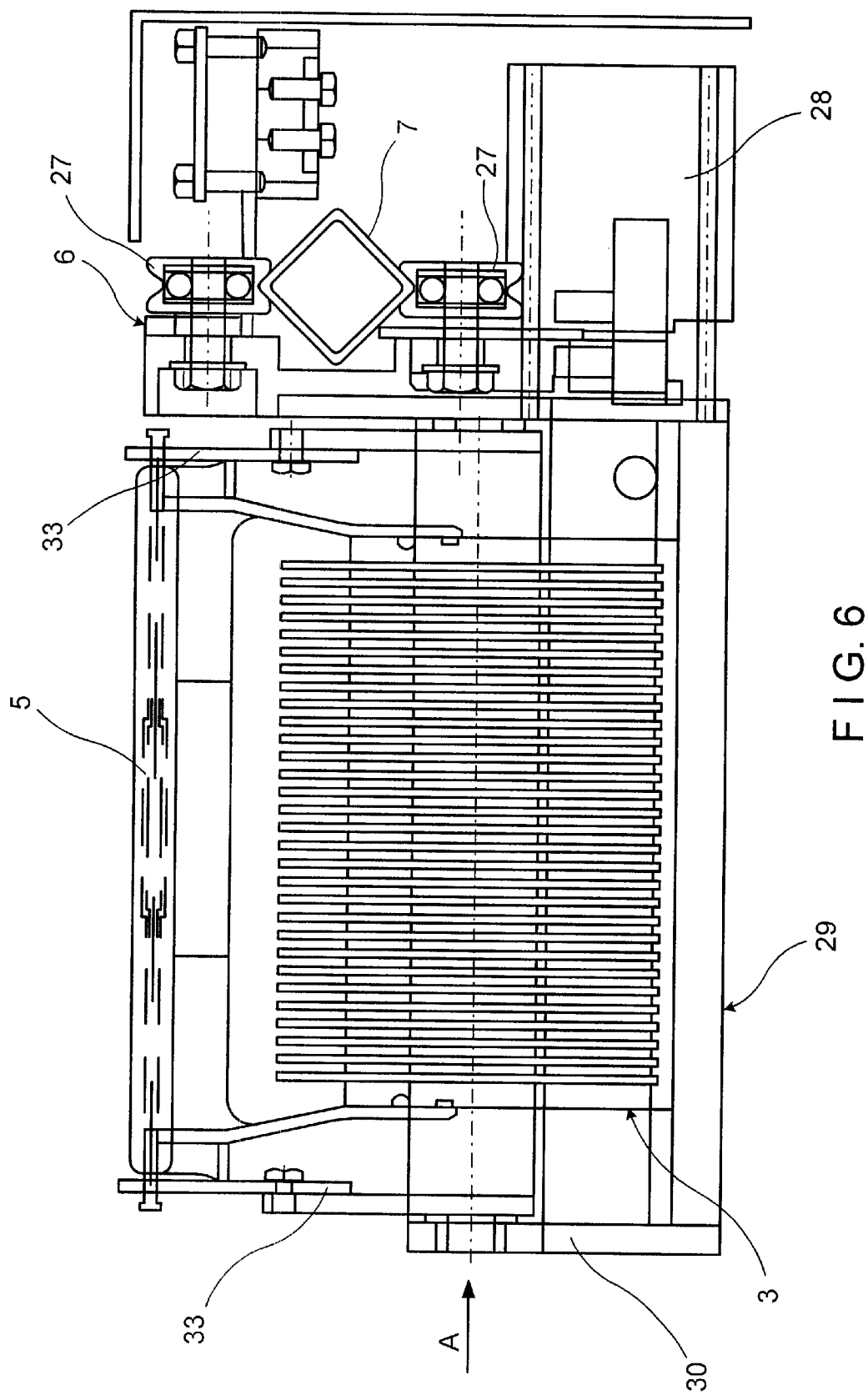
FIG. 6 shows a view of the transport means and of a basket with microscope slides lifted thereby, shown in a manner corresponding to that of FIGS. 4 and 5, but on an enlarged scale to show structural details.

An embodiment of the conveyor 6 is schematically shown in FIG. 6, together with a lifted basket 3 with microscope slides, and parts of the conveyor are shown on an enlarged scale in FIGS. 7A–7D.

As appears from these figures, the conveyor 6 comprises a triangular carriage bracket 26 wherein a carriage wheel 27 is mounted at each corner, so that the wheels rest against and run along the aforementioned inclined guide 7. As shown, the inclined guide is in the form of a square rail where two of the wheels rest against an upper edge of the rail and the third wheel rests against a lower edge of the rail, the wheels having a peripheral recess which is adapted to rest against the rail. one of the wheels is driven by a motor 28, for movement of the conveyor back and forth along the guide rail 7 in accordance with the topical program.

The conveyor further is provided with a transport carriage 29 for transport of the baskets 3 in the apparatus. The transport carriage comprises side gables 30 and a tight bottom 31. For lifting of baskets 3 with microscope slides 4 from the respective vessels there is arranged a U-shaped lifting stirrup or clamp 32 having angularly bent arms 33 which, in a central portion, are mounted at the upper ends of the side gables 30 of the transport carriage 29. The lifting clamp 32 is rotatable by means of engine drive, and the lifting arms 33 at their free ends are provided with a notch 34 for engagement with the suspension means 5 on a basket which is to be lifted.

When lifting a basket 3, this takes place as shown in FIGS. 7A–7D, so that the basket with turning of the lifting clamp 32 is lifted in a circular movement, the free ends of the arms 33 following a circular path in accordance with the shown arrow C. Simultaneously with this turning, the lifting clamp performs a linear movement, the conveyor being moved somewhat back and forth in accordance with the arrow L in FIG. 7D. The circular and linear movements of the lifting clamps are adapted in such a manner in relation to each other that the basket moves upwards and sideways inwards towards an edge of the vessel 2, so that an edge 35 of the basket strokes along an upper edge 36 of the vessel. Thereby excess liquid from the basket is wiped off against the edge of the vessel, to reduce transfer of liquid 37 from the bath in the basket to the next bath.

With further turning of the lifting clamp 32, the basket 3 is moved sideways onto the transport carriage 29 where it is supported by the tight bottom plate 31 of the carriage, and the microscope slides will be standing in sideways contact with the bottom plate. Thereby it is achieved that possible additional liquid from the microscope slides is collected in the transport carriage and is not transferred to other baths when the basket is lifted off the carriage.

What is claimed is:

1. A staining apparatus for preparation of tissue specimens placed on microscope slides, comprising a plurality of working stations in the form of vessels having liquid baths for receiving baskets or suspensions receiving microscope slides with the topical specimens, a means for transport of each of the baskets/suspensions to respective working stations to undergo a staining process, a control unit for controlling the staining process in accordance with a chosen program, and a magazine arranged for initial loading and simultaneous reception of a chosen number of baskets/suspensions with microscope slides, the magazine being provided with a means for heating of the baskets/suspensions in the magazine before said transport to the working stations.

2. An apparatus according to claim 1, wherein the heating means is arranged to be controlled by the control unit in accordance with the topical program.

3. An apparatus according to claim 1, wherein the heating means comprises a heating element and a fan, the fan being arranged for blowing of hot air towards baskets/suspensions placed in the magazine.

4. An apparatus according to claim 1, wherein the magazine comprises a magazine housing having a wall facing the stations and being provided with a door which can be opened and closed automatically when inputting and outputting baskets/suspensions by the transport means.

5. An apparatus according to claim 4, wherein the magazine comprises an inner framework for support of baskets/suspensions, the framework being automatically raisable and lowerable between a lower and an upper position.

6. An apparatus according to claim 1, wherein the transport means is arranged to bring a ready basket to a delivery position for direct delivery to an operator.

7. An apparatus according to claim 1, wherein the transport means is arranged to lift a basket from a vessel at a station in a circular movement, so that excess liquid from the basket during said movement is wiped off towards an edge of the vessel.

* * * * *